United States Patent [19]

Cuckle et al.

[11] Patent Number: 5,716,853
[45] Date of Patent: Feb. 10, 1998

[54] PRENATAL DOWN SYNDROME SCREENING WITH ASSAYS SPECIFIC FOR UGP

[75] Inventors: Howard S. Cuckle, North Yorkshire, United Kingdom; Roger P. Walker, Benicia, Calif.

[73] Assignee: Chiron Diagnostics Corporation, Medfield, Mass.

[21] Appl. No.: 647,437

[22] Filed: Apr. 30, 1996

Related U.S. Application Data

[60] Provisional application No. 60/000,945, Jul. 7, 1995.

[51] Int. Cl.$^6$ .................. G01N 33/76; G01N 33/577; C07K 14/59
[52] U.S. Cl. .................. 436/510; 436/814; 435/7.1; 435/7.72; 435/7.9; 435/7.92; 435/7.93; 435/7.94; 435/7.95; 530/398
[58] Field of Search .................. 435/7.1, 7.72, 435/7.9, 7.92–7.95; 530/398; 436/510, 814

[56] References Cited

U.S. PATENT DOCUMENTS

| | | | |
|---|---|---|---|
| 5,240,912 | 8/1993 | Jodaro . | |
| 5,356,817 | 10/1994 | Cole | 436/64 |
| 5,445,968 | 8/1995 | Blithe et al. | 436/510 |

FOREIGN PATENT DOCUMENTS

| | | | |
|---|---|---|---|
| 0421392 | 4/1991 | European Pat. Off. | 5/20 |
| 9002759 | 3/1990 | WIPO | 33/76 |
| 9403804 | 2/1994 | WIPO | 33/49 |

OTHER PUBLICATIONS

Canick and Knight, "Multiple-marker Screening for Fetal Down Syndrome."*Contemporary OB/GYN*, pp. 3–12 (Apr. 1992).

Ciba Corning Diagnostics Corp., "Triton®UGP EIA Kit" Brochure (May. 1995).

Cole, L.A., "β-Core Fragment (β-Core, UGP or UGF)", *Tumour Marker Update*, 6(3) : 69–75 (1994).

Cole et al., "The Deactivation of hCG by Nicking and Dissociation."*Journal of Clinical Endocrinology and Metabolism*, 76(3) : 704–710 (1993).

Cole et al., "Urine hCG β-Subunit Core Fragment, a Sensitive Test for Ectopic Pregnancy", *Journal of Clinical Endocrinology and Metabolism*, 78(2) : 497–499 (1994).

Cuckle, H., "Screening at 11–14 weeks of gestation: the role of established markers and PAPP-A."*Screening of Down's Syndrome*, Ed. Grudzinskas et al., pp. 311–323 [Cambridge University Press; Cambridge, U.K. (1994)].

Cuckle et al., "Maternal Urine —A Possibility for use in Screening", Screening News (European Down's Syndrome Screening Group Newsletter), 1(2): 5 (Jul. 1994).

Cuckle et al., "Urinary β–Core Human Chorionic Gonadotropin: A New Approach to Down's Syndrome Screening, "*Prenatal Diagnosis*, 14: 953–958 (Oct. 1994).

Hayashi and Kozu, "Maternal Urinary β–core Fragment of hCG/Creatinine Ratios and Fetal Chromosomal Abnormalities in the Second Trimester of Pregnancy."*Prenatal Diagnosis*,15: 11–16 (Jan. 1995).

Kato and Braunstein, "β–Core Fragment Is a Major Form of Immunoreactive Urinary Chorionic Gonadotropin in Human Pregnancy."*J. Clin. Endocrinol. Metab.*,66: 1197–1201 (1988).

Lee et al., "The purification and development of a radioimmunoassay forβ–core fragment of human chorionic gonadotrophin in urine: application as a marker of gynaecological cancer in premenopausal and postmenopausal women, "*J. Endocrinal*,130: 481–489 (1991).

Cuckle, et al., "Urinary β–Core Human Chorionic Gonadotropin: A New Approach to Down's Syndrome Screening", *Prenatal Diagnosis*,vol. 14: 953–958 Ciba–Corning Diagnosis Corp. Triton®UGP EIA Kit, May. 1995.

Akar, et al., "A radioimmunoassay for the core fragment of the human choronic gonadotrophin β–subunit."*J. Endocrinology and Metabolism*,vol. 66, pp.538–545, 1988.

Spencer , et al., "Fills βhCG as First Trimester marker for fetal tusing."The Lancet, vol. 339, p.1480, 1992.

O'Connor et al., "Development of Highly Sensitive Immunoassays to Measure Human Chroionic Gonadotropin."its βsubunit and βCore Fragment in the urine; application to malignancies, *Cancer Research*,vol 48, pp. 1361–1366, 1988.

O'Connor et al., "Recent Advances in the Chemistry and Immunochemistry of Human Chorionic Gonadotropin: Impact on Clinical Measurements."*Endocrine Reviews*, 15(5): 650–683 (1994).

Spencer et al., "Urine Free Beta hCG and Beta Core in pregnancies affected by Trisomy 21."*Am. Soc. Hum. Genet.*, 57: A289 (Oct.1995) (Abstract).

*Primary Examiner*—Michael P. Woodward
*Assistant Examiner*—Brenda Glass Brumback
*Attorney, Agent, or Firm*—Leona L. Lauder; Arthur S. Morgenstern

[57] ABSTRACT

Herein disclosed are methods for prenatally assessing risks of a pregnancy being affected by Down syndrome by testing maternal urine samples for levels of urinary gonadotropin peptide (UGP) elevated above normal. The methods employ immunoassays that are highly specific for UGP and have molar cross-reactivities of less than about 10% with intact hCG, with β-subunit hCG, and with α-subunit hCG. The immunoassay methods of this invention are useful to test first trimester maternal urine samples. Among other benefits, first trimester prenatal screening provides the opportunity to terminate the pregnancy at an early gestational age, in the case of an unfavorable outcome.

26 Claims, No Drawings

PRENATAL DOWN SYNDROME SCREENING WITH ASSAYS SPECIFIC FOR UGP

This application claims the benefit of U.S. Provisional Application No. 60/000,945 filed Jul. 7, 1995 which is entitled "Urinary Screening for Down's Syndrome and Other Aneuploidies."

FIELD OF THE INVENTION

The present invention is in the field of prenatal diagnosis. It concerns non-invasive methods to screen prenatally for fetal Down syndrome by immunoassays employing antibodies that are specific for urinary gonadotropin peptide (UGP) [also known as β-core or urinary gonadotropin fragment (UGF)].

BACKGROUND OF THE INVENTION

Trisomy 21, commonly known as Down syndrome, is characterized by an extra copy of chromosome 21. People afflicted with Down syndrome have severe mental retardation, reduced life expectancies, and abnormal immune responses that predispose them to serious infections as well as thyroid autoimmunity. Further, 40% of Down syndrome patients have congenital heart disease and a 10 to 20-fold increased risk of developing leukemia over the general population. All Down syndrome patients older than 40 develop neuropathological changes characteristic of Alzheimer's disease.

Prenatal tests to detect aneuploidy, such as trisomy 21, by amniocentesis or chorionic villus sampling (CVS) have been available since the late 1960s. Amniocentesis is the most common invasive prenatal diagnostic procedure. In amniocentesis, amniotic fluid is sampled by inserting a hollow needle through the mother's anterior abdominal and uterine walls into the amniotic cavity by piercing the chorion and amnion. It is usually performed in the second trimester of pregnancy. CVS is performed primarily during the first trimester, and involves collecting cells from the chorion which develops into the placenta.

Another invasive prenatal diagnostic technique is cordocentesis or percutaneous umbilical cord blood sampling, commonly known as fetal blood sampling. Fetal blood sampling involves obtaining fetal blood cells from vessels of the umbilical cord, and is often performed about the 20th gestational week.

Amniocentesis is used selectively because it presents a risk of about 1% of inducing spontaneous abortion. CVS and fetal blood sampling carry a similar or higher risk of inducing abortion, and there is also concern that these procedures may lead to fetal limb malformations in some cases. Thus, amniocentesis, CVS and fetal blood sampling are procedures that are only employed if a pregnancy is considered at high risk for a serious congenital anomaly. Thus, some means is required to select those pregnancies that are at a significant risk of Down syndrome to justify the risks of such invasive prenatal diagnostic procedures, as amniocentesis, CVS and fetal blood sampling.

Prior to 1983, the principal method for selecting pregnancies that had an increased risk for Down syndrome was based on maternal age, that is, the older the age of the mother, the higher the risk that the pregnancy would be affected by Down syndrome. In 1974, biochemical screening for neural tube defects by measuring alpha-fetoprotein (AFP) began. In 1984, the use of the AFP screen was additionally adopted for the detection of Down syndrome. Since the early 1990s, a multiple marker blood test has been used to screen for this disorder. A common version of this test is the three marker triple test. The triple screen measures AFP, human chorionic gonadotropin (hCG) and unconjugated estriol ($uE_3$) in the serum of pregnant women.

The triple screen provides a means to screen the population of pregnant women to determine which pregnancies are at risk for Down syndrome and other serious genetic defects. The risk is calculated based on the results of the screen, along with other cofactors, such as, maternal age, to determine if the risk is high enough to warrant an invasive diagnostic procedure, such as, amniocentesis, CVS or fetal blood sampling. Such prenatal screens, as the triple screen, can be used either to reduce the need for amniocentesis or to increase Down syndrome detection for the same amount of amniocentesis. "The efficiency of the Triple test is projected to be one case of fetal Down syndrome detected for every 50 amniocenteses performed." [Canick and Knight, "Multiple-marker Screening for Fetal Down Syndrome," Contemporary OB/GYN, pp. 3–12 (April 1992).]

Although pregnant women who are 35 years or older are the standard high risk group for fetal Down syndrome, screening also needs to be applied to young women because although they are at lower risk, most affected pregnancies are in young women. Approximately 80% of babies born with Down syndrome are born to mothers under 35. ["Down Syndrome Screening Suggested for Pregnant Women under 35, "*ACOG Newsletter,* 38(8): 141 (August 1994).]

The triple screen combines the analysis of three markers from serum to reduce false positive results (which result in the performance of unnecessary invasive procedures) and false negatives (in which serious genetic defects, such as, trisomy 21, go undetected). In women under 35, the double screen (AFP and hCG) can pick up about half of Down syndrome cases and a large proportion of other chromosome defects during the second trimester. The triple screen (AFP, hCG and $uE_3$) increases the detection rate by 5–10% of Down syndrome and a further increase in the detection of all other serious chromosome defects, thus decreasing the number of false-positives. Such rates mean that the double and triple screens still fail to detect a significant number of Down syndrome affected pregnancies.

Although the triple screen has a suggested screening period of 15 to 20 weeks gestation, such screening has been recommended between weeks 16–18 to maximize the window for spinal bifida detection. [Canick and Knight, supra (April 1992).] A 1992 survey of prenatal maternal serum screening for AFP alone or for multiple analyses reported that very few such screenings occurred in the thirteenth or earlier week of gestation. [Palomaki et al., "Maternal Serum Screening for Fetal Down Syndrome in the United States: A 1992 Survey," *Am. J. Obstet. Gynecol.,* 169(6): 1558–1562 (1992).] The triple screen thus suffers from the additional problem that once a risk of Down syndrome is predicted, and amniocentesis or another invasive prenatal definitive diagnostic procedure is performed to diagnose Down syndrome, it is at an advanced date of gestation, when termination of a pregnancy can be more physically and emotionally trying for the mother, and when certain less traumatic abortion procedures, such as, vacuum curettage, may not be available.

The limitations of the triple screen and the adverse consequences of unnecessary, potentially harmful and expensive invasive prenatal diagnostic procedures, such as, amniocentesis, have led to a search for more discriminatory markers for prenatal Down syndrome screening. Cuckle et al., "Urinary β-Core Human Chorionic Gonadotropin: A New Approach to Down's Syndrome Screening," *Prenatal Diagnosis*, 14: 953–958 (October 1994), pointed out on page 953 that "[h]uman chorionic gonadotropin (hCG) is the most discriminatory maternal serum marker of Down's syndrome. . . . [and] carried out a study to establish whether urinary β-core-hCG [an alternative name for UGP], a major metabolic product of hCG, might be even a better marker."

Human chorionic gonadotropin (hCG) is a glycopeptide hormone produced by the syncytiotrophoblasts of the fetal placenta that is thought to maintain the function of the corpus luteum during the first few weeks of pregnancy, to promote steroidogenesis in the fetoplacental unit, and to stimulate fetal testicular secretion of testosterone. It can be detected by immunoassay in the maternal urine within days after fertilization and thus provides the basis of the most commonly used pregnancy tests. The intact hCG molecule is a dimer comprising a specific β subunit covalently bound to an e subunit, which is common to other glycoproteins.

Urinary gonadotropin peptide (UGP) has an amino acid sequence related to the β-subunit of hCG. UGP is comprised of β-subunit residues 6 through 40 attached by disulfide linkages to residues 55 through 92. UGP is glycosylated but lacks the sialic acid and O-linked carbohydrate residues present on hCG β subunit.

UGP has been found in the urine of pregnant women carrying normal fetuses, and also in the urine of patients with gestational trophoblastic and non-trophoblastic malignancies [Cole et al., "Urinary Human Chorionic Gonadotropin Free B-subunit and B-core Fragment: A New Marker of Gynecological Cancers," *Cancer Res.*, 48: 1356–1360 (1988); Cole et al., "Urinary Gonadotropin Fragments (UGF) in Cancers of the Female Reproductive System," *Gynecol. Oncol.*, 31: 82–90 (1988); O'Connor et al., "Development of Highly Sensitive Immunoassays to Measure Human Chorionic Gonadotropin, Its β-subunit, and β-core Fragment in the Urine: Application to Malignancies," *Cancer Res.*, 48: 1361–1366 (1988); and Akar et al, "A Radioimmunoassay for the Core Fragment of the Human Chorionic Gonadotropin β-subunit," *J. Clin. Endocrinol. and Metab.*, 66: 538–545 (1988).] UGP has also been found to be associated with certain ovarian cancers. [Cole and Nam, "Urinary Gonadotropin Fragment (UGF) Measurements in the Diagnosis and Management of Ovarian Cancer," *Yale J. Bio. and Med.*, 62: 367–378 (1989).]

Cuckle et al., supra examined UGP levels in second trimester samples from singleton pregnancies affected and unaffected by Down syndrome and compared the levels. A radioimmunoassay was used in the Cuckle et al. study as described in Lee et al., "The purification and development of a radioimmunoassay for β-core fragment of human chorionic gonadotrophin in urine: application as a marker of gynaecological cancer in premenopausal and postmenopausal women," *J. Endocrinol*, 130: 481–489 (1991). That "assay has a partial mole per mole cross-reaction with intact hCG (6.9 per cent) and free β-hCG (18 per cent) but negligible cross-reactivity with free α subunit . . . ." [Cuckle et al. at page 954.]

Cuckle et al. showed that UGP levels are elevated on average in the second trimester of pregnancies affected by fetal Down syndrome and may be reduced in the presence of other serious, but less common aneuploidies. The observed median level in Down syndrome (6.11 MOM; 95% confidence interval 3.7 to 10.0) was greater than the corresponding median level for intact hCG in maternal serum (2.0 MOM; 1.9–2.1) and free β-hCG (2.3 MOM; 2.1–2.5).

There are important advantages to using urinalysis for prenatal screening for Down syndrome. Urine tests are less expensive than serum testing, avoid the safety issues and handling risks associated with the collection and storage of blood samples, as well as the invasiveness and discomfort of phlebotomy. Urine samples can be easily collected and shipped, if necessary, where women have limited access to medical testing facilities because of geography or socioeconomic status. UGP is stable to changes in temperature, pH, and storage time at −20° and 40° C.

However, the β-core fragment assay described in Cuckle et al., supra had elevated levels in Down syndrome affected pregnancies only in samples taken between the 19th week and the 22nd week plus 4 days of gestation. As indicated above, there are disadvantages to second trimester testing, in that delays in confirming a fetal Down syndrome diagnosis result in more traumatic abortion procedures being necessitated. Also, the emotional attachment and expectations of the pregnant woman and her family for a healthy baby, grow during the pregnancy, making the abortion decision more difficult later in the gestational term.

The instant invention provides the benefits of urinalysis and avoids the problems of second trimester prenatal screening by providing methods to screen first trimester urine samples for fetal Down syndrome. The prenatal screening methods of the instant invention are highly specific for UGP and minimally cross-reactive with intact hCG, with β-subunit hCG and with α-subunit hCG.

SUMMARY OF THE INVENTION

The instant invention provides methods for prenatally determining whether there is a high risk of a pregnancy being affected by Down syndrome by testing maternal urine samples for elevations of urinary gonadotropin peptide (UGP) levels above normal. The methods employ immunoassays that are specific for UGP and have molar cross-reactivities of less than about 10% with intact hCG, with β-subunit hCG, and with α-subunit hCG. Preferably the immunoassay methods of this invention have a molar cross-reactivity of less than about 5%, more preferably less than about 3%, and still more preferably less than about 1%, with intact hCG, with β-subunit hCG, and with α-subunit hCG.

The UGP level in the maternal urine sample is related to the median for unaffected pregnancies, and the degree of elevation or reduction indicates the risk of Down syndrome. Results from the prenatal screening methods of this invention are generally expressed as multiples of the median value (MOM) for unaffected pregnancies of the same gestation. Exemplary positive results from the screening methods according to this invention are those wherein the UGP level is from about 1.1 MOM to higher multiples, from about 1.5 MOM to higher multiples, from about 2 MOM and higher multiples.

Such a screening result is used to assess the fetal Down syndrome risk either alone or in conjunction with results from other screening tests with other serum and/or urinary markers, and/or other factors, such as, maternal age, maternal health, maternal weight among other factors. For example, maternal age and UGP levels are independent predictors of Down syndrome risk, as is true for each of the commonly used serum markers. Therefore, after performing the prenatal screening methods of this invention, the risk of a Down syndrome affected pregnancy can be calculated by multiplying the age-related risk by a likelihood ratio derived from the UGP level found in the maternal urine sample in relation to control samples.

Other urinary markers which could be preferred for assessing the risk of a Down syndrome affected pregnancy in conjunction with UGP levels, include pregnancy-associated plasma protein A (PAPP-A), dimeric inhibin, total estrogen (tE), unconjugated estriol (uE$_3$), total estriol (tE$_3$), AFP and proform of eosinophilic major basic protein (proMBP), among other urinary marker possibilities.

In general, a positive result from the screening methods of this invention is an indicator that a more invasive prenatal diagnostic procedure, such as, amniocentesis, CVS or fetal blood sampling, should be performed to determine definitively whether the pregnancy is affected with Down syndrome.

Gestation-specific medians for UGP can be calculated by weighted non-linear regression from the values for control urine samples. To account for variations in the concentrations of urine samples, UGP levels can be expressed in terms of creatinine. Gestational ages of cases and controls can be determined by ultrasound parameters and by last menstrual period dating.

The control samples are preferably taken from a population of pregnant women that are matched as well as practicable to the population from which the pregnant woman who provided the test sample comes. For example, population parameters could include race, ethnicity, and geographical location, among other parameters.

The prenatal screening methods of this invention are useful to test first trimester maternal urine samples. Thereby the screening methods of this invention provide prenatal screening results at a significantly earlier date than had heretofore been available. The benefits of such earlier screening results are discussed above in the Background.

Generally, maternal urine samples can be taken for testing, according to this invention, during the fifth week to the 14th completed week, that is, 14 weeks plus six days, of gestation. Preferably, maternal urine samples can be taken for testing during the sixth week to the 14th completed week of gestation; more preferably during the seventh week to the 14th completed week of gestation; still more preferably during the eighth week to the 14th completed week of gestation; further preferably, during the ninth week to the 14th completed week of gestation; alternatively, during the 10th week to the 14th completed week of gestation; further alternatively during the ninth week to the 13th week of gestation; and still further also preferably from the ninth week to the twelfth completed week of gestation.

Other preferred gestational periods from the first trimester, during which maternal urine samples can be taken for testing according to this invention include the following: the gestational periods from the beginning of the seventh week to the end of the 14th week; from the beginning of the eighth week to the end of the 14th week; from the beginning of the ninth week to the end of the 14th week; from the beginning of the tenth week to the end of the 14th week; from the beginning of the fifth week to the end of the 13th week; from the beginning of the fifth week to the end of the 12th week; from the beginning of the sixth week to the end of the 13th week; from the beginning of the sixth week to the end of the 12th week; from the beginning of the seventh week to the end of the 13th week; from the beginning of the seventh week to the end of the 12th week; from the beginning of the eighth week to the end of the 13th week; from the beginning of the eighth week to the end of the 12th week; from the beginning of the eighth week to the end of the 11th week; from the beginning of the eighth week to the end of the 10th week; from the beginning of the ninth week to the end of the 11th week; from the beginning of the ninth week to the end of the 10th week; from the beginning of the tenth week to the end of the 13th week; and from the beginning of the tenth week to the end of the twelfth week.

The immunoassay methods of this invention employ UGP standards. Blithe et al., U.S. Pat. No. 5,445,968 (issued Aug. 29, 1995) discloses methods of purifying UGP.

The prenatal screening methods of this invention can be in any standard immunoassay format, for example, a competitive radioimmunoassay, a sandwich EIA or sandwich radioimmunoassay, among other known formats. A sandwich assay is a preferred format of this invention, and a sandwich EIA is a further preferred embodiment.

The prenatal screening methods of this invention can be automated. A preferred automated immunoassay system is Ciba Corning Diagnostic Corp.'s (CCD's) ACS-180™ Automated Chemiluminescence System [CCD; Medfield, Mass. (USA)].

The prenatal screening methods of this invention employ antibodies, that are defined herein to include whole antibodies or biologically active fragments of antibodies. The antibodies used in the immunoassay methods can be monoclonal and/or polyclonal, preferably monoclonal and/or affinity-purified polyclonal antibodies. The specificity of the immunoassay methods is provided by antibodies which specifically bind to UGP; generally such antibodies are monoclonal antibodies.

Tracer antibodies that can be used in the immunoassay methods of this invention can be directly or indirectly linked to a detectable marker. The signal from said marker can indicate the level of UGP in the sample tested. The signal's intensity may be directly proportional to the level of UGP in the sample.

Exemplary detectable markers can be selected from the group consisting of radionuclides, fluorescers, bioluminescers, chemiluminescers, dyes, enzymes, coenzymes, enzyme substrates, enzyme cofactors, enzyme inhibitors, enzyme subunits, metal ions, and free radicals.

Antibodies used in the immunoassay methods may be linked to a solid phase, for example, the wall of a container or the surface of magnetic or paramagnetic particles, among other solid phases.

DETAILED DESCRIPTION

The following abbreviations are used herein:

Abbreviations

AFP—alpha-fetoprotein
BL—bioluminescent
CCD—Ciba Corning Diagnostics Corp.
CL—chemiluminescent
CVS—chorionic villus sampling
EIA—enzyme immunoassay
fmol—femtomole
hCG—human chorionic gonadotropin
HRP—horseradish peroxidase
L—liter
LNMP—last normal menstrual period
mg—milligram
ml—milliliter
mmol—millimole
MOM—multiples of normal gestation-specific median
ng—nanogram
PAPP-A—pregnancy-associated plasma protein A
pmol—picomole
PMP—paramagnetic particle
proMBP—proform of eosinophilic major basic protein
SD—standard deviation tE—total estrogen
TMB—tetramethyl benzidine
uE3—unconjugated estriol
UGP—urinary gonadotropin peptide Definitions Alternative terms used in the art for urinary gonadotropin peptide (UGP) are β-core fragment, β-core-hCG, and urinary gonadotropin fragment (UGF).

The first trimester is herein defined as 14 completed weeks (14 weeks, 6 days) from the onset of a pregnant woman's last normal menstrual period (LNMP).

Intact hCG is a term that defines hCG in its dimeric form when its α and β subunits are covalently bound together.

Total hCG is a term that includes intact hCG and either its free α subunit or its free β subunit.

"Aneuploidy" is defined herein as any deviation from an exact multiple of the haploid number of chromosomes, whether fewer (hypoploidy, as in Turner syndrome) or more (hyperploidy, as in Down syndrome).

The term "antibodies" is defined herein to include not only whole antibodies but also biologically active fragments of antibodies, preferably fragments containing the antigen binding regions.

Representative Embodiments

Herein are disclosed methods for prenatally assessing risks of a pregnancy being affected by Down syndrome by testing maternal urine samples for elevations above normal of urinary gonadotropin peptide (UGP). The methods employ immunoassays that are highly specific for UGP and have molar cross-reactivities of less than about 10% with intact hCG, with β-subunit hCG, and with α-subunit hCG.

Urinary gonadotropin peptide (UGP), also known as β-core or urinary gonadotropin fragment (UGF), was first detected in 1977 by Good et al. ["Molecular Forms of Human Chorionic Gonadotropin Serum, Urine and Placental Extracts," *Fertil. Steril.*, 28: 846–850 (1977)]. UGP was characterized by Wehmann and Nisula ["Characterization of a Discrete Degradation Product of Human Chorionic Gonadotropin Beta Subunit in Humans," *J. Clin. Endocrinol. Metab.*, 51: 101–105 (1980)] and by Birken et al., ["The Structure of the Human Chorionic Gonadotropin Beta Core Fragment from Pregnancy Urine," *Endocrinol.*, 123: 572–573 (1980)].

UGP is a peptide with a molecular weight of 10.4 kilodaltons (kd). As indicated in the Background, supra, UGP has an amino acid sequence related to the β-subunit of human chorionic gonadotropin (hCG).

Unlike hCG which is measured in maternal sera, the UGP assay is based on levels found in maternal urines corrected for creatinine excretion to control for dilution variability. Levels are expressed as multiples of the normal gestation-specific median (MOM).

One preferred embodiment of the prenatal screening methods of this invention is expressed as follows.

A method for prenatally determining whether there is a significant risk of a pregnancy being affected by Down syndrome comprising:

(a) taking a maternal urine sample;
(b) testing said maternal urine sample to determine the level of UGP in said sample with an immunoassay that is specific for UGP and has a molar cross-reactivity of less than about 10% with each of the following: intact hCG, β-subunit hCG, and with α-subunit hCG;
(c) determining whether the level of UGP in said sample is elevated above a level of UGP that is normal in urine samples from women whose pregnancies are unaffected by aneuploidy, and whose pregnancies are at about the same gestational age as the pregnancy under analysis; and
(d) determining that there is a significant risk of fetal Down syndrome if the level of UGP in said sample is elevated above said normal level.

As indicated in the Summary of the Invention, supra the immunoassay specific for UGP preferably has molar cross-reactivities of less than 5% with intact hCG, with β-subunit hCG, and with α-subunit hCG; more preferably those cross-reactivities are less than 3%; and still more preferably those cross-reactivities are less than 1%.

A preferred immunoassay for use in the prenatal screening methods of this invention is commercially available from CCD. That assay is Triton® UGP EIA Kit from Ciba Corning Diagnostics Corp. (CCD: Alameda, Calif.; USA). The CCD assay exhibits the following molar cross-reactivities: hCG, 0.11 per cent; free beta subunit of hCG, 0.043 per cent, and free alpha subunit of hCG, 0.009 per cent.

Other exemplary immunoassays can comprise, for example, antibodies described in Blithe et al., U.S. Pat. No. 5,445,868 (issued Aug. 29, 1995).

In a preferred embodiment of the invention, monoclonal antibodies specific to UGP are coupled to paramagnetic particles (PMP) and incubated with the urine sample to be tested. The immobilized complex is washed to remove unbound materials. Anti-UGP antibodies conjugated with a chemiluminscent tag, preferably acridinium ester (AE), are then incubated with the immunocomplex immobilized on the PMP. A step to separate bound tracer from the unbound tracer is then performed. The bound fraction is then incubated with the light reagent and the amount of light photons generated is determined in a luminometer, such as, for example, the Ciba Corning ACS-180™ Automated Chemiluminescent System [Ciba Corning Diagnostics Corp. (CCD) E. Walpole, MA (USA)], further described infra. The values obtained are directly proportional to the concentration of UGP in the urine sample.

The embodiments outlined above are representative of a wide number of assay methods that can be used in accordance with this invention. There are many variations and modifications of such outlined embodiments within the skill of one in the art.

It would also be apparent to one of skill in the art that the immunoassay methods of this invention can be in a variety of formats, such as, sandwich assays, competition assays, bridge immunoassays, among other formats well known to those of skill in the art. [See, for example, U.S. Pat. Nos. 5,296,347; 4,233,402; 4,034,074; and 4,098,876.]

Variations of the representative embodiments of the methods of this invention within conventional knowledge of those of skill in the art are considered to be within the scope of the instant invention. Preferred variations and more detailed embodiments are identified in the following sections.

Reference is made hereby to standard textbooks of immunology that contain methods for carrying out various immunoassay formats that can be adapted from those specifically represented herein. See, for example, *Molecular Biology and Biotechnology: A Comprehensive Desk Reference* (Ed. R. A. Meyers) [VCH Publishers, Inc., New York, N.Y. (1995)]; Moore and Persaud, *The Developing Human: Clinically Oriented Embryology*, 5th Edition [W. B. Saunders Company; Philadelphia/London/Toronto/Montreal/Sydney/Tokyo (1993)]; Darnell et al., *Molecular Cell Biology*, W. H. Freeman and Company (N.Y. 1990); Colowick et al., *Meth-* ods in *Enzymology*, Volume 152 [Academic Press, Inc. (London) Ltd. (1987)]; and Goding J. W., *Monoclonal Antibodies: Principles and Practice: Production and Application of Monoclonal Antibodies in Cell Biology, Biochemistry, and Immunology* [Academic Press Inc. (London) Ltd.; 1983.]

Urine Concentration

The prenatal screening methods of this invention do not require uniformity in the volume of urine obtained from each pregnant woman of the control or case groups or the time of voiding. The UGP concentration can be corrected for creatinine, for example, expressed in nmol/mmol creatinine.

The CCD UGP kit expresses UGP levels as pmol per mg urinary creatinine. UGP concentrations may be reported in International Units as mmol UGP/L and expressed as mmol/mmol creatinine as exemplified in Example 2, infra.

Creatinine content in urine can be measured by the Jaffe method using a Monarch 200 centrifugal analyser as described in Cuckle et al., *Prenatal Diagnosis*, 14: 953–958 (1994). Creatinine levels can also be measured on a Synchron CX-5 chemistry analyser (Beckman Instruments; Brea, Calif., USA).

Other Markers

"Population screening is the identification, among apparently healthy individuals, of those who are sufficiently at risk of a specific disorder to justify a subsequent diagnostic test or procedure. This implies the testing of all pregnancies in order to identify those few at a great enough risk to warrant an invasive diagnostic procedure, such as amniocentesis." [Canick et al., "Maternal Serum Screening for Aneuploidy and Open Fetal Defects," *Prenatal Diagnosis*, 20(3): 443 (September 1993).] A positive result from a screen indicates a higher risk of fetal Down syndrome, and a negative result does not necessarily mean that a fetus is free of Down syndrome but that the fetus is at a lower risk of the syndrome.

Screening detection rates can be increased and false positives can be decreased by combining the results of a prenatal screening method with results of screening with other markers and assessing the results in conjunction with other factors. When considering the cost of a second or third marker, it has to be weighed against the extra costs incurred without their use in additional amniocentesis tests for the affected pregnancies. [Cuckle, H. S., *Clin. Chem.*, 38(9): 1687–1689 (1992).]

As indicated above in the Summary of the Invention, the results from the prenatal screening methods of this invention can be used alone or in conjunction with results from other screening tests with other serum and/or urinary markers, and/or other factors, such as, maternal age, maternal health, maternal weight, among other factors to assess the risks of a pregnancy being affected by Down syndrome. For example, maternal age and UGP level are independent predictors of Down syndrome risk, as is true for each of the commonly used serum markers.

Other markers which could be preferred urinary markers for assessing the risks of a Down syndrome affected pregnancy include PAPP-A, dimeric inhibin, tE, $uE_3$, AFP and proMBP, among other urinary marker possibilities. Particularly preferred potential urinary markers to be used in conjunction with UGP to assess fetal Down syndrome risks are PAPP-A, dimeric inhibin and tE.

PAPP-A may be found in first trimester urine samples, preferably taken during the ninth to the 13th completed week of gestation, at levels significantly reduced below normal in Down syndrome affected pregnancies.

An assay for dimeric inhibin is described in Cuckle et al., "Maternal Serum Inhibin Levels in Second-Trimester Down's Syndrome Pregnancies," *Prenatal Diagnosis*, 14: 387–390 (1994). That assay could be adapted for urine testing. Dimeric inhibin may be useful in the first trimester.

Total estrogen can be measured by a continuous flow system based on the Kober reaction [Lever et al., "Improved estriol determination in a continuous flow system," *Biochem. Med.*, 8: 188–198 (1973)]. Total estrogen could be measured as μmol/mmol creatinine.

Antibodies

As indicated above, the term "antibodies" is defined to include not only whole antibodies but also biologically active fragments of antibodies, preferably fragments containing the antigen binding regions. Such antibodies may be prepared by conventional methodology and/or by genetic engineering.

Antibody fragments may be genetically engineered, preferably from the variable regions of the light and/or heavy chains (VH and VL), including the hypervariable regions, and still more preferably from both the VH and VL regions. For example, the term "antibodies" as used herein comprehends polyclonal and monoclonal antibodies and biologically active fragments thereof including among other possibilities "univalent" antibodies [Glennie et al., *Nature*, 295: 712 (1982)]; Fab proteins including Fab' and F(ab')2 fragments whether covalently or non-covalently aggregated; light or heavy chains alone, preferably variable heavy and light chain regions (VH and VL regions), and more preferably including the hypervariable regions [otherwise known as the complementarity determining regions (CDRs) of said VH and VL regions]; Fc proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., *PNAS* (USA), 79: 6409 (1982)].

It may be preferred for many immunoassays of this invention that biologically active fragments rather than whole antibodies be used. Fab fragments are particularly preferred fragments in accordance with this invention to avoid non-specific binding.

Antibodies for use in the instant invention can be genetically engineered. [See, for example, Morrison et al., *Clin. Chem.*, 34: 1668 (1988); Morrison and Oi, *Adv. Immunol.*, 44: 65 (1989); Rodwell, *Nature* 342: 99 (1989); Pluckthun, A., *Nature*, 347: 497 (1990); Winter and Milstein, *Nature* 349: 293 (1991); Pluckthun, A., *Bio/Technology*, 9: 545 (1991); Wetzel, R., *Protein Eng.*, 4: 371 (1991); Geisow, M. J., *Trends Biotechnol.* 10: 75 (1992); and Chiswell and McCaffery, *Trends Biotechnol.* 10 85 (1992).] Further bispecific and other types of antibodies [for example, Lerner and Tramanto, *Trends Biochem. Sci.*, 12: 427 (1987); Shokat and Schultz, *Annu. Rev. Immunol.*, 8: 335 (1990); Schultz, P. G., *Science*, 240: 426 (1988); Benkavic et al., *Science*, 250: 1135 (1990); and Lerner et al., *Science* 252: 659 (1991); Noland and O'Kennedy, *Biochem. Biophys. Acta.* 1040: 1 (1990); and Bolhuis et al., *Cell Biochem.*, 47: 306 (1991)] can also be used according to this invention.

Standards

Purified reference preparations can be obtained by established procedures. [See, for example, Blithe et al., "Purification of β-core fragment from pregnancy urine and demonstration that its carbohydrate moieties differ from those of native human chorionic gonadotropin-β," *Endocrinol.*, 122: 173–180 (1988).]

Automated Immunoassay System

The methods of this invention can be readily adapted to automated immunochemistry analyzers. To facilitate automation of the methods of this invention and to reduce the turnaround time, anti-UGP antibodies may be coupled to magnetizable particles.

A preferred automated/immunoassay system is the Ciba Corning ACS:180™ Automated Chemiluminescence System [CCD; Medfield, Mass. (USA)]. The Ciba Corning ACS:180™ Automated Immunoassay System is described in Dudley, B. S., *J. Clin. Immunoassay,* 14(2): 77 (Summer 1991). The system uses chemiluminescent labels as tracers and paramagnetic particles as solid-phase reagents. The ACS:180 system accommodates both competitive binding and sandwich-type assays, wherein each of the steps are automated. The ACS:180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester.

Solid Phase

The solid phase used in the assays of this invention may be any surface commonly used in immunoassays. For example, the solid phase may be particulate; it may be the surface of beads, for example, glass or polystyrene beads; or it may be the solid wall surface of any of a variety of containers, for example, centrifuge tubes, columns, microtiter plate wells, filters, membranes and tubing, among other containers.

When particles are used as the solid phase, they will preferably be of a size in the range of from about 0.4 to 200 microns, more usually from about 0.8 to 4.0 microns. Magnetic or magnetizable particles such as, paramagnetic particles (PMP), are a preferred particulate solid phase, and microtiter plate wells are a preferred solid wall surface. Magnetic or magnetizable particles may be particularly preferred when the steps of the methods of this invention are performed in an automated immunoassay system.

Preferred detection/quantitation systems of this invention may be luminescent, and a luminescent detection/quantitation system in conjunction with a signal amplification system could be used, if necessary. Exemplary luminescent labels, preferably chemiluminescent labels, are detailed below, as are signal amplification systems.

Signal Detection/Quantitation Systems

The complexes formed by the assays of this invention can be detected, or detected and quantitated by any known detection/quantitation systems used in immunoassays. As appropriate, the antibodies of this invention used as tracers may be labeled in any manner directly or indirectly, that results in a signal that is visible or can be rendered visible.

Detectable marker substances include radionuclides, such as $^3$H, $^{125}$I, and $^{131}$I; fluorescers, such aas, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, α-, β-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immuno- complex formed. Exemplary of enzyme substrate combinations are horseradish peroxidase and tetramethyl benzidine (TMB), and alkaline phosphatase and paranitrophenyl phosphate (pNPP).

Preferred detection, or detection and quantitation systems according to this invention produce luminescent signals, bioluminescent (BL) or chemiluminescent (CL). In chemiluminescent (CL) or bioluminescent (BL) assays, the intensity or the total light emission is measured and related to the concentration of the analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, Vargulla and Renilla. Luminol can be used optionally with an enhancer molecule, preferably selected from the group consisting of 4-iodophenol or 4-hydroxy-cinnamic acid. Acridinium esters are one of the preferred types of CL labels according to this invention. A signal is generated by treatment with an oxidant under basic conditions.

Also preferred luminescent detection systems are those wherein the signal is produced by an enzymatic reaction upon a substrate. CL and BL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g. AMPPD or CSPD; [Kricka, L. J., "Chemiluminescence and Bioluminescence, Analysis by," at p. 167, *Molecular Biology and Biotechnology: A Comprehensive Desk Reference* (ed. R. A. Meyers) (VCH Publishers; N.Y., N.Y.; 1995)]; preferably a disodium salt of 4-methoxy-4-(3-phosphatephenyl)spiro [1,2-dioxetane-3,2'-adamantane], with or without an enhancer molecule, preferably, 1-(trioctylphosphonium methyl)-4-(tributylphosphonium methyl) benzene diochloride. HRP is preferably used with substrates, such as, 2',3',6'-trifluorophenyl 3-methoxy-10-methylacridan-9-carboxylate.

CL and BL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between the antibody and the marker, or the use of well known signal amplification signals, such as, using a biotinylated antibody complexed to UGP and then adding strepavidin conjugated to HRP and then TMB.

Exemplary of binding pairs that can be used to link antibodies of assays of this invention to detectable markers are biotin/avidin, streptavidin, or anti-biotin; avidin/anti-avidin; thyroxine/thyroxine-binding globulin; antigen/ antibody; antibody/anti-antibody; carbohydrate/ lectins; hapten/anti-hapten antibody; dyes and hydrophobic molecules/hydrophobic protein binding sites; enzyme inhibitor, coenzyme or cofactor/enzyme; polynucleic acid/ homologous polynucleic acid sequence; fluorescein/anti-fluorescein; dinitrophenol/ anti-dinitrophenol; vitamin B12/ intrinsic factor; cortisone, cortisol/cortisol binding protein; and ligands for specific receptor protein/membrane associated specific receptor proteins. Preferred binding pairs according to this invention are biotin/avidin or streptavidin, more preferably biotin/streptavidin.

Various means for linking labels directly or indirectly to antibodies are known in the art. For example, labels may be bound either covalently or non-covalently. Exemplary antibody conjugation methods are described in: Avarmeas et al., Scan. J. Immunol., 8 (Suppl. 7): 7 (1978); Bayer et al., Meth. Enzymol., 62: 308 (1979); Chandler et al., J. Immunol. Meth., 53: 187 (1982); Ekeke and Abuknesha, J. Steroid Biochem., 11: 1579 (1979); Engvall and Perlmann, J. Immunol., 109: 129 (1972); Geoghegan et al., Immunol. Comm., 7: 1 (1978); and Wilson and Nakane, Immunofluorescence and Related Techniques, p. 215 [Elsevier/North Holland Biomedical Press; Amsterdam (1978)].

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

The following examples are presented to help in the better understanding of the subject invention and are for purposes of illustration only. The examples are not to be construed as limiting the invention in any manner.

EXAMPLE 1

In this example, one maternal urine sample from a Down syndrome affected pregnancy at the gestational age of 12 weeks, 0 days, as determined by ultrasound, was assayed for UGP according to the methods of this invention. [The case sample (karyotype: 47, XX, +21) was kindly provided by Nancy C. Rose, M.D. of the Department of Obstetrics and Gynecology at the Hospital of the University of Pennsylvania (Pa., USA).] The reason for the prenatal diagnosis has advanced maternal age.

Six controls from gestational ages plus or minus one week from that of the Down syndrome case sample were tested by the same method to establish the MOM. [Five of the control samples and one other sample were kindly provided respectively by Britta Stirnal, M.D. (Germany), and Leonard H. Kellner, M.S. (Montefiore Medical Center, Albert Einstein College of Medicine; New York, N.Y. USA). The tests and analyses were performed by or under the direction of Leonard H. Kellner, M.S. (Montefiore Medical Center) and Jacob A. Canick, Ph.D. (Women and Infants Hospital, Brown University School of Medicine; Providence, R.I., USA).]

Case and control samples were stored at −20° C. for from 1 week to 8 months prior to assay. While the fetal karyotype of the control samples was not always known, it was assumed that none of the controls was from an aneuploid pregnancy. Gestational age of the control samples were determined by either ultrasound parameters or by last menstrual period dating.

The Triton® UGP EIA Kit from Ciba Corning Diagnostics (Alameda, Calif.; U.S.A.) was used to determine the UGP levels in the case and control samples. The protocol used for the assay was essentially as provided with the kit but appropriate dilutions for the first trimester samples were made. The assay range for UGP was 0.4–16.0 fmol/ml. Because of the high levels of UGP in the maternal urine samples, the samples prior to assay were diluted 50,000 to 100,000 (50 k to 100 k) with diluent provided with the kit as indicated in the results shown in Table 1.

UGP levels were ultimately expressed as pmol per mg urinary creatinine to account for variations in the concentration of the urine samples. There had been no attempt to control the time of day that the urine samples were taken. Creatinine levels were measured on a Synchron CX-5 chemistry analyser (Beckman Instruments; Brea, Calif.; USA).

TABLE 1

| Samples | gest. age | creatinine mg/ml | UGP raw (fmol/ml) | dilution factor | UGP (pmol/ml) | UGP (pol/mg creat) |
|---|---|---|---|---|---|---|
| Control 1 | 13,2 | 1.01 | 2.34 | 100 K. | 234.0 | 231.7 |
| Control 2 | 11,6 | 0.63 | 1.48 | 50 K. | 74.0 | 117.5 |
| Control 3 | 12,1 | 0.52 | 2.54 | 50 K. | 127.0 | 244.2 |
| Control 4 | 11,4 | 1.10 | 4.05 | 50 K. | 202.5 | 184.1 |
| Control 5 | 11,0 | 0.90 | 3.06 | 50 K. | 153.0 | 170.0 |
| Control 6 | 12,0 | 1.04 | 0.83 | 50 K. | 41.5 | 39.9 |
| Case: | | | | | | |
| Down Syndrome Case | 12,0 | 1.60 | 6.24 | 100 K. | 624.0 | 390.0 |

The control values ranged from 39.9 to 244.2 pmol UGP per mg creatinine. The median value for the six controls was 177 pmol per mg creatinine. The level of UGP in the Down syndrome case was 390 pmol UGP per mg creatinine. Thus, the result for this case expressed as multiples of the control median (MOM) was 390/177=2.20 MOM, i.e., slightly more than twice the control median, a positive result.

EXAMPLE 2

In this example, seven first trimester maternal urine samples from Down syndrome affected pregnancies, that is, seven case samples, and 214 first trimester control urine samples were assayed for UGP. The assay protocol with the Triton UGP EIA (CCD; Alameda, Calif.; USA) kit used was essentially as described above in Example 1. However, the samples were diluted 10,000-fold with the kit diluent, and if the UGP levels were still too high for the kit's assay range, a repeat assay was done at a higher dilution.

Dilutions were performed with a Hamilton Microlab 100 semi-automatic diluter. The concentrations reported in this example are in mmol UGP/L and expressed as mmol/mmol creatinine.

Controls

A regression curve from the UGP/creatinine values for the 214 control samples from pregnancies of 9 to 13 weeks gestation was prepared. The following quadratic equation basically describes the data:

$$a + bx + cx^2 + dx^3$$

wherein x represents the gestational age in days; and wherein the coefficients are as follows:

a=−527.7;
b=19.13;
c=−0.2230; and
d=0.0008558.

The observed versus the fitted values were as follows:

| Gestational Week | No. of Samples | Observed | Fitted |
|---|---|---|---|
| 9 | 12 | 9.9758 | 9.4130 |
| 10 | 18 | 12.6759 | 13.5389 |
| 11 | 77 | 14.5134 | 13.7500 |
| 12 | 29 | 11.4615 | 12.5007 |
| 13 | 78 | 10.9880 | 10.9107 |

There appeared to be a peak urinary UGP level at about 11 weeks and then a decline in the levels thereafter.

MOMs in unaffected pregnancies. The spread of the MOM values for unaffected pregnancies are exemplified as follows.

| Controls | UGP MOM |
|---|---|
| 10th centile | 0.41 |
| Median | 0.99 |
| 90th centile | 1.95 |

Assuming a Gaussian distribution, the SD of log UGP based on the 10th–90th range would be 0.26, which is similar to that of free beta hCG in serum.

Down Syndrome Affected Pregnancies

The results of testing the seven urine samples from the Down syndrome affected pregnancies are expressed below as multiples of the gestation-specific median (MOM) and shown below in Table 2. Case No. 3 is from a twin pregnancy discordant for Down syndrome.

TABLE 2

| Down Syndrome Case No. | Gestational Age in Weeks | MOM |
|---|---|---|
| (1) | 10 | 1.90215 |
| (2) | 11 | 0.34949 |
| (3) (twin) | 12 | 2.65054 |
| (4) | 12 | 0.92861 |
| (5) | 12 | 2.79836 |
| (6) | 12 | 0.49450 |
| (7) | 13 | 1.71604 |

Four out of the seven case samples extremely elevated, namely Case Nos. 1, 3, 5 and 7. The distribution in Down syndrome cases may be bimodal with the low values being from non-viable pregnancies. About one-half of first trimester Down syndrome affected fetuses are non-viable.

Two of the urine samples—Case Nos. 3 and 7—were taken after CVS. The remainder were prospective samples taken before CVS or any other invasive prenatal diagnostic procedure was performed.

The mean approximated the observed log median of the seven cases, the log of 1.72 MOM or 0.24. The observed SD of log UGP is 0.36.

Covariables

There appears to be no correlation between the UGP concentrations in the first trimester urine samples with the following covariables: maternal age (r=0.04615 based on 72 samples); maternal weight (r=−0.21217 based on 65 samples); serum AFP (r=0.02184 based on 67 samples); and serum uE3 (r=0.00305 based on 67 samples). However, there appears to be a statistically significant correlation between the urinary UGP levels and serum free beta hCG levels, although the correlation coefficient is very low (r=0.42888 based on 67 samples; p=0.0003).

The descriptions of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to best explain the principles of the invention and its practical application to enable thereby others skilled in the art to best utilize the invention in various embodiments and with various modifications as are suited to the particular use contemplated. It is intended that the scope of the invention be defined by the claims appended hereto.

All references cited herein are hereby incorporated by reference.

What we claim is:

1. A method for prenatally determining whether there is a significant risk of a pregnancy being affected by Down syndrome comprising:
   (a) taking a maternal urine sample during the first trimester of said pregnancy;
   (b) testing said maternal urine sample to determine the level of UGP in said sample with an immunoassay that is specific for UGP and has a molar cross-reactivity of less than about 10% with each of the following: intact hCG, β-subunit hCG, and α-subunit hCG;
   (c) determining whether the level of UGP in said sample is elevated above a level of UGP that is normal in urine samples from women whose pregnancies are unaffected by aneuploidy, and whose pregnancies are at about the same gestational age as the pregnancy under analysis; and
   (d) determining that there is a significant risk of fetal Down syndrome if the level of UGP in said sample is elevated above said normal level.

2. The method according to claim 1 wherein said immunoassay has a molar cross-reactivity of less than about 5% with each of the following: intact hCG, β-subunit of hCG, and α-subunit hCG.

3. The method according to claim 1 wherein said immunoassay has a molar cross-reactivity of less than about 3% with each of the following: intact hCG, β-subunit hCG, and α-subunit hCG.

4. The method according to claim 1 wherein said immunoassay has a molar cross-reactivity of less than about 1% with each of the following: intact hCG, β-subunit hCG, and α-subunit hCG.

5. The method according to claim 1 wherein said maternal urine sample was taken during the fifth week to the 14th completed week of said pregnancy.

6. The method according to claim 5 wherein said maternal urine sample was taken during the fifth week to the 13th completed week of said pregnancy.

7. The method according to claim 5 wherein said maternal urine sample was taken during the sixth week to the 14th completed week of said pregnancy.

8. The method according to claim 5 wherein said maternal urine sample was taken during the seventh week to the 14th completed week of said pregnancy.

9. The method according to claim 5 wherein said maternal urine sample was taken during the eighth week to the 14th completed week of said pregnancy.

10. The method according to claim 5 wherein said maternal urine sample was taken during the ninth week to the 14th completed week of said pregnancy.

11. The method according to claim 5 wherein said maternal urine sample was taken during the 10th week to the 14th completed week of said pregnancy.

12. The method according to claim 5 wherein said maternal urine sample was taken during the ninth week to the thirteenth completed week of said pregnancy.

13. The method according to claim 5 wherein said maternal urine sample was taken during the ninth week to the twelfth completed week of said pregnancy.

14. The method according to claim 1 wherein said immunoassay is in a sandwich assay format or in a competitive assay format.

15. The method according to claim 1 wherein said immunoassay is automated.

16. The method according to claim 1 wherein the level of UGP in said sample is elevated above said normal level to a statistically significant extent.

17. The method according to claim 1 wherein the level of UGP in said sample is two or more times the level of UGP that is normal for pregnancies unaffected by aneuploidy at about the same gestational age as the pregnancy sample under analysis.

18. The method according to claim 1 wherein the UGP levels are corrected for variability in urine concentrations by being expressed relative to creatinine content in said urine samples.

19. A method according to claim 1 wherein said immunoassay comprises the use of monoclonal antibodies and/or affinity-purified polyclonal antibodies that bind specifically to UGP.

20. A method according to claim 1 wherein said immunoassay comprises the use of antibodies directly or indirectly linked to a detectable marker, and wherein signal from said marker indicates the level of UGP, and said signal's intensity is directly proportional to the level of UGP in said sample.

21. The method according to claim 20 wherein said immunoassay further comprises the use of antibodies linked to a solid phase.

22. The method according to claim 20 wherein said detectable marker is selected from the group consisting of radionuclides, fluorescers, bioluminescers, chemiluminescers, dyes, enzymes, coenzymes, enzyme substrates, enzyme cofactors, enzyme inhibitors, enzyme subunits, metal ions, and free radicals.

23. The method according to claim 22 wherein the detectable marker is either selected from the group consisting of acridinium esters, acridinium sulfonyl carboxamides, fluorescein, luminol, umbelliferone, isoluminol derivatives, photoproteins, and luciferases, or is produced by an enzymatic reaction upon a substrate.

24. The method according to claim 20 wherein the detectable marker is either an acridinium ester or is produced by an enzymatic reaction with a chemiluminescent substrate and an enzyme selected from the group consisting of alkaline phosphatase, glucose oxidase, glucose 6-phosphate dehydrogenase, α, β-galactosidase, horseradish peroxidase, and xanthine oxidase.

25. The method according to claim 21 wherein said solid phase comprises magnetic or paramagnetic particles.

26. The method according to claim 25 wherein said immunoassay is automated, and wherein said detectable marker is an acridinium ester.

* * * * *